United States Patent [19]
Gottschalk et al.

[11] Patent Number: 5,164,309
[45] Date of Patent: Nov. 17, 1992

[54] PROCESS FOR THE MICROBIOLOGICAL PREPARATION OF 1,3-PROPANE-DIOL FROM GLYCEROL BY CITROBACTER

[75] Inventors: G. Gottschalk, Nörtenhardenberg; Beate Averhoff, Gottingen, both of Fed. Rep. of Germany

[73] Assignee: Unilever Patent Holdings B.V., Rotterdam, Netherlands

[21] Appl. No.: 448,137

[22] Filed: Dec. 12, 1989

[30] Foreign Application Priority Data

Dec. 12, 1988 [EP] European Pat. Off. ........ 88120718.7

[51] Int. Cl.$^5$ .............................................. C12P 7/18
[52] U.S. Cl. .................................. 435/158; 435/252.1
[58] Field of Search ...................... 435/157, 158, 252.1

[56] References Cited

PUBLICATIONS

Johnson et al., "Inactivation of Glycerol Dehydrogenase of *Klebsiella pneumoniae* and the Role of Divalent Cations", *J. Bacteriology*, vol. 164, No. 1, pp. 479–483, 1985.

Schütz et al., "Anaerobic Reduction of Glycerol to Propanediol-1.3 by *Lactobacillus brevis* and *Lactobacillus buchneri*", *System. Appl. Microbiol.* vol. 5, pp. 169–178, 1984.

Streekstra et al., "Overflow metabolism during anaerobic growth of *Klebsiella aerogenes* NCTC 418 on glycerol and dihydroxyacetone in chemostat culture", *Arch. Microbiol.*, vol. 147, pp. 268–275, 1987.

*Primary Examiner*—Douglas W. Robinson
*Assistant Examiner*—Marian C. Knode
*Attorney, Agent, or Firm*—Cushman, Darby & Cushman

[57] ABSTRACT

A process of the microbiological preparation of 1,3 propane diol from glycerol in growth media of suitable bacterial strains is described, accompanied by the addition of a cosubstrate in the form of a H-donor and the separation of the propane diol formed. It is characterized in that a) biomass is formed in a growth phase from the selected bacterial strain and accompanied by feeding with glycerol and, if necessary, while substantially excluding the H-donor until a stationary growth phase occurs and b) further glycerol and H-donor matched to the biomass are added to the resulting stationary cell suspension for increased 1,3-propane diol formation. This process makes it possible to produce 1,3-propane diol in a high yield from glycerol with a small amount of unobjectionable by-products in a batchwise manner or in continuous form, following immobilization.

12 Claims, 2 Drawing Sheets

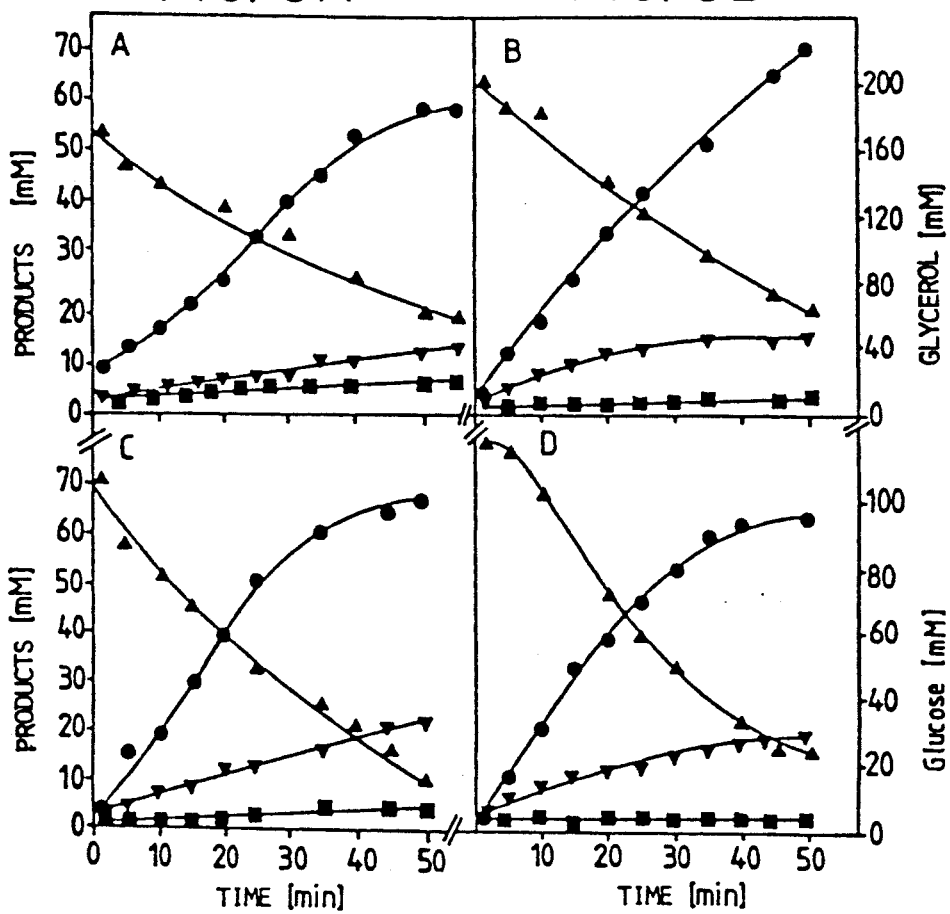
FIG. 3A  FIG. 3B
FIG. 3C  FIG. 3D
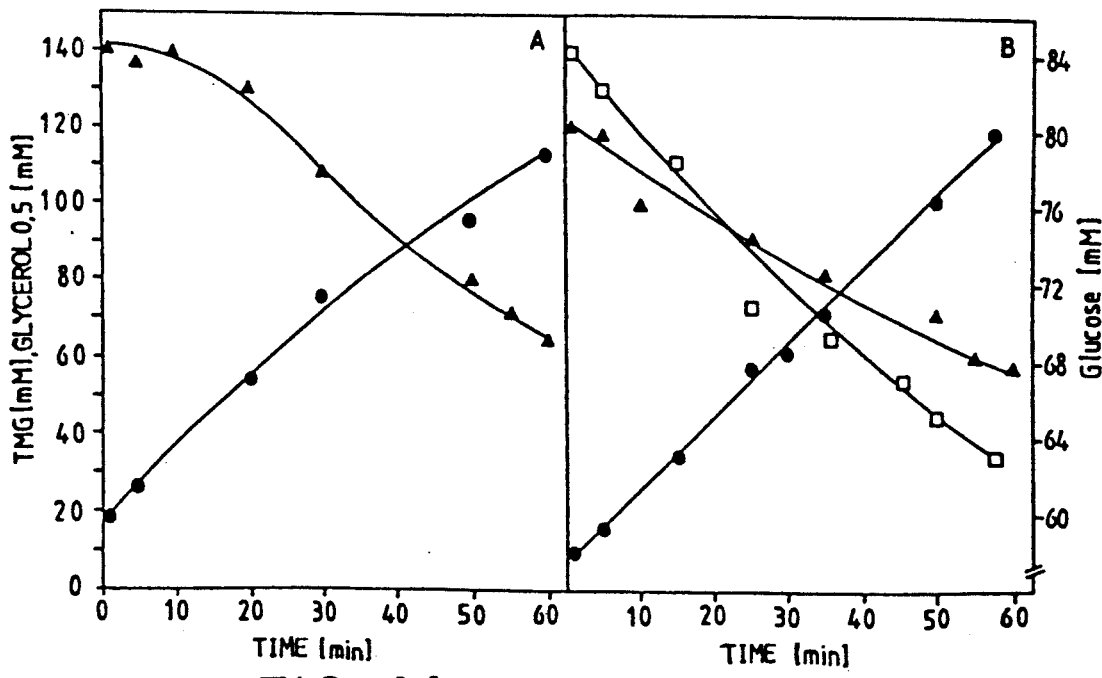
FIG. 4A  FIG. 4B

PROCESS FOR THE MICROBIOLOGICAL PREPARATION OF 1,3-PROPANE-DIOL FROM GLYCEROL BY CITROBACTER

The invention relates to a process for the microbiological preparation of 1,3-propane diol from glycerol in growth media of suitable bacterial strains, accompanied by the addition of a cosubstrate as the H-donor and the separation of the propane diol formed.

BACKGROUND OF THE INVENTION

Processes for the preparation of 1,3-propane diol or trimethylene glycol (TMG) from glycerol are known. When performing these, essentially the following points must be taken into consideration. Bacterial strains able to convert glycerol into 1,3-propane diol are found e.g. in the species *Klebsiella* (cf. *J. Bacteriol.*, 1982, 149, 413-419), *Citrobacter* (cf. *J. Bacteriol.*, 1944, 39, 409-415), *Clostridium* (cf. *Appl. Environ. Microbiol.*, 1987, 53, 639-643), *Ilyobacter* (cf. *Arch. Microbiol.*, 1984, 140, 139-146) and *Lactobacillus* (cf. *System. Appl. Microbiol.*, 1984, 5, 169-178). It cannot be excluded that further obligatory or optional ferments also form 1,3-propane diol as a fermentation product. Within the *Citrobacter* species, *C. freundii* is particularly well known as a 1,3-propane diol producer. Several strains (e.g. DSM 30039, 30040 and 30047) are available.

As a function of the bacterial strain used, it is possible to employ mineral media with glycerol or complex media with glycerol for the growth and associated production of 1,3-propane diol. The ambient conditions, such as the pH and temperature, are also dependent on the strain used. Preference is always given to anaerobic growth conditions, because the enzymes for the transformation of glycerol into 1,3-propane diol are only formed under anaerobic conditions. An adequate cobalt iron supply to the bacteria must be ensured, because the participating enzyme glycerol dehydratase contains coenzyme $B_{12}$ (cf. *Arch. Biochem. Biophys.*, 1962, 97, 538-543).

Using the aformentioned bacterial strains, 1,3-propane diol can be produced batchwise or continuously. As a function of the species, different 1,3-propane diol yields are obtained in the batchwise anaerobic fermentation of glycerol: 78% for *Lactobacillus buchneri*, 61% for *Clostridium butylicum*, 40% for *Ilyobacter polytropus* and 50% for *Citrobacter freundii*. In connection with the *Lactobacillus* species, it must be borne in mind that a mixture of glycerol and glucose (2:1) and not glycerol alone can be fermented. As a function of the bacterial species during the fermentation of glycerol different by-product spectra appear, mainly acetate, butyrate, lactate, formate, succinate, ethanol, butanol and hydroxypropionate (in the case of *Ilyobacter polytropus*).

Whereas the aforementioned fermentations relate to cultures operating in a batchwise manner, in 1987 results were published for the first time concerning a continuous fermentation of glycerol for the production of 1,3-propane diol (cf. *Appl. Environ. Microbiol.*, 1987, vol. 53, 639-643). Fermentation was carried out with *Clostridium butylicum* B 593, an obligatory ferment. 3.8% glycerol were added to the chemically defined medium and 97% thereof were reacted by the bacteria. It was also necessary to add 0.2% yeast extract to the medium. In the gas phase there was oxygen-free carbon dioxide, the residence time of the bacteria in the reactor was 10 hours and the temperature 35° C. Continuous fermentation gave the following product spectrum analyzed with HPLC and GC: 61% 1.3-propane diol, 6.6% acetate, 1.6% butyrate, 0.9% lactate, 0.6% butanol and 0.6% ethanol.

On the basis of the above statements, a 1,3-propane diol synthesis without by-products does not appear to be possible with bacteria, because part of the glycerol must be oxidized in order to obtain energy, whilst the reduction of glycerol to 1,3-propane diol is used for eliminating hydrogen which occurs. On lowering the pH-value from 6.5 to 4.9 the growth of bacteria and 1,3-propane diol production are reduced. An intermediate during the synthesis of 1,3-propane diol is 3-hydroxypropionaldehyde, whose production was also the aim of certain fermentation tests (cf. *Appl. Environ. Microbiol.*, 1983, vol. 46, No. 1, 62-67). In the case of anaerobic fermentation of glycerol with *Klebsiella pneumoniae*, the speed of enzymatic reaction was displaced through the addition of semicarbazide hydrochloride. 3-hydroxypropionaldehyde production took place much more rapidly than the subsequent reduction to 1,3-propane diol and consequently led to a 3-hydroxypropionaldehyde accumulation. In the case of 30 g/l glycerol solutions, a 3-hydroxypropionaldehyde yield of 13.1 g/l was obtained.

SUMMARY OF THE INVENTION

The problem of the invention is to so improve the aforementioned process that it permits a simple, economic, rapid and continuous preparation of 1,3-propane diol from glycerol with a high yield and whilst substantially excluding environmentally prejudicial by-products.

According to the invention this problem is solved in that a) biomass is formed from the selected bacterial strain, accompanied by feeding with glycerol and, if necessary, with a substantial exclusion of the H-donor in a growth phase until a stationary growth phase is obtained and b) for increased 1,3-propane diol formation, to the corresponding stationary cell suspension are added further glycerol and a H-donor matched to the biomass.

Thus, the essence of the inventive process is that initially in a process stage a) biomass is formed until a stationary growth phase or cell suspension has been obtained. It is necessary for most of the bacterial strains usable with the scope of the invention to substantially exclude a H-donor in said process stage a). This more particularly applies for the strains *Citrobacter freundii*, *Klebsiella pneumoniae*, *Clostridium autobutylicum* and *Clostridium butylicum*. However, several bacterial strains exist which, in the growth phase, grow in the presence of a H-donor and possibly even have a need for the latter, such as e.g. *Lactobacillus brevis* and *Lactobacillus buchneri*. However, the growth of most of the bacterial strains which can be used according to the invention is disturbed by the presence of a H-donor, so that in such cases the latter should be substantially excluded. This must also be borne in mind in connection with the qualitative evaluation of the glycerol-containing starting materials. Thus, if the glycerol starting material already contained a significant sugar fraction, such as glucose, then said fraction could be responsible for disturbing process stage a). Otherwise there are no significant limitations on the inventive process with regards to the glycerol starting material. Thus, it can e.g. be glycerol splitting water from high pressure splitting, or glycerol water from soap splitting, or glycerol water from the methanolysis of fats or oils, e.g. from fish oil, coconut oil or palm kernel oil.

BRIEF DESCRIPTION OF THE DRAWINGS

FIGS. 1 through 4 illustrate graphically various aspects of the invention.

FIG. 1 shows the TMG production from glycerol in an ammonium limited static culture in the presence of 11 times increased $CO^{+2}$ concentration.

FIG. 2 shows the course of TMG production through cell suspension while keeping the pH-value constant using KOH titrations.

FIG. 3 shows a comparison of TMG production from glycerol from stationary cells at different pH-value.

FIG. 4 shows a comparison of TMG production from a glycerol through stationary cells in the presence or absence of glucose.

DESCRIPTION OF PREFERRED EMBODIMENT OF THE INVENTION

Figure 1:
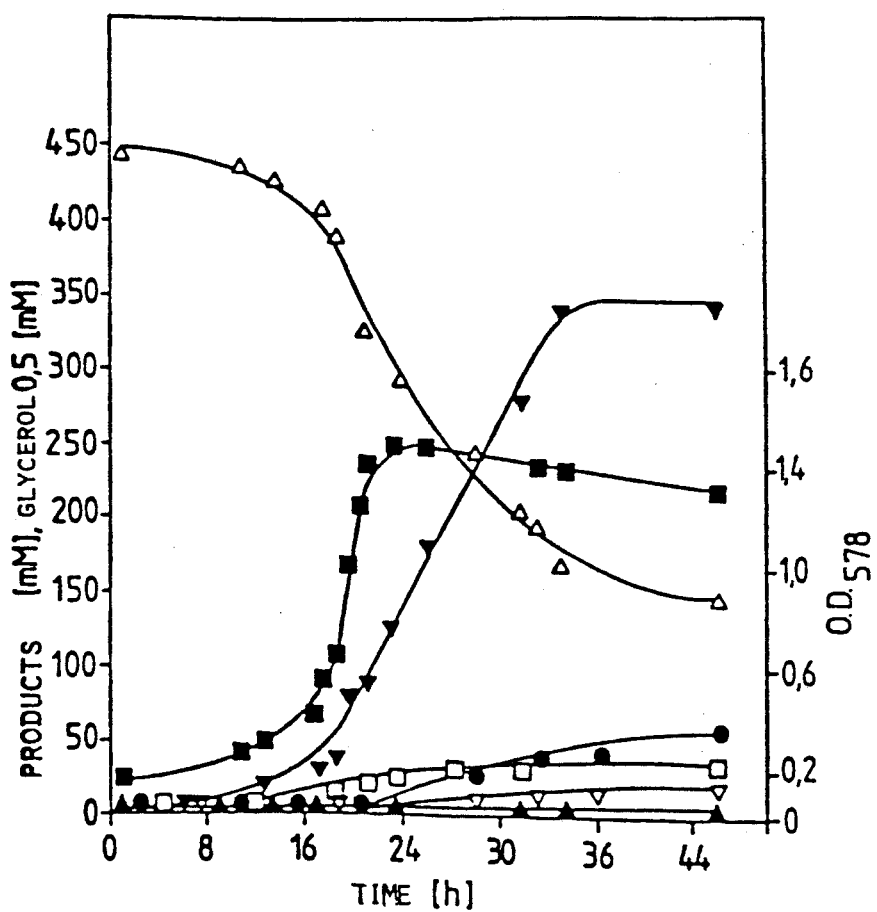

The above explanations apply regarding the choice of the suitable bacterial strain. Representatives of the Citrobacter species, such as Citrobacter freundii, are used in a particularly advantageous manner. The strains DSM 30039, 30040 and 30041 are particularly suitable.

In process stage a), it is appropriate to adopt the following procedure: the description relating to Citrobacter freundii DSM 30040, but the remarks correspondingly apply to other bacterial strains. A mineral solution is prepared, in the manner known to the expert. However, as a special feature it contains a cobalt salt, such as in particular cobalt chloride in high concentration (250–550 µg $CoCl_2$/l) and an ammonium salt, such as in particular ammonium sulphate, as the growth-limiting N-source. As a function of the desired biomass concentration, the ammonium sulphate concentration can be approximately 0.4 to 1.5 g/l. Following the addition of glycerol (e.g. approximately 0.3 mol/l and a preculture of strain DSM 30040, incubation takes place at approximately 37° C. under anaerobic conditions. After about 12 to 20 hours (at 0.3 mol/l), the growing culture enters the stationary phase necessary for process stage b).

The concentration of the glycerol in process stage a) is not critical. It could be in a wide range, e.g. approximately 0.001 to 1 mol/l, although this range can also be exceeded. The range of approximately 0.1 to 0.4 mol/l is preferred, in particular approximately 0.3 mol/l.

It is not critical for performing process stage a) whether it is performed anaerobically or aerobically. It is preferably performed anaerobically, so that the enzymes particularly suitable for the desired conversion of glycerol into 1,3-propane diol are formed in an optimum manner. When process stage a) has allowed the desired biomass quantity to form, measures are taken to end the growth. This is preferably brought about in that the end of growth is controlled by adding a predetermined quanitity of a phosphate or nitrogen source. Ammonium salts, such as ammonium sulphate, have proved to be particularly advantageous.

The inventive process can be performed both in a complex medium and in a mineral medium. Preference is given to the mineral medium, because it is less expensive, easier to handle and easier to dispose of at the end of the process. A mineral medium is understood to mean a medium, which only contains inorganic salts and additionally glycerol and possibly cystein (as the reducing agent). The complex medium differs therefrom through a content of preferably approximately 1% yeast extract.

The biomass obtained according to process stage a) can be directly supplied to process stage b). It is also advantageous to concentrate the biomass by centrifuging or to immobilize it. Immobilization can take place in various ways, such as e.g. by calcium alginate, carageenan or polyurethanes. Immobilization preferably takes place with the readily available, commercial calcium alginate (Protanal-LF-20/60). The immobilized form of the biomass can e.g. be filled into a column, to which is continuously supplied the glycerol solution to be treated. This leads to the particular advantage of continuous process performance, the biomass being usable for weeks and without impairing its efficiency for obtaining 1,3-propane diol from glycerol. Tests have been carried out in which the biomass was active, without deterioration, for more than 42 days.

Glycerol is not essential for feeding the microorganisms for process stage b) and instead the combination glycerol/H-donor should be used. There are no significant limitations regarding the choice of the H-donor. The expert will instead choose the H-donor on the basis of his knowledge and the chosen bacterial strain. Generally, the H-donor can be constituted by mono-saccharides and disaccharides, particularly fructose and glucose. Glucose has proved particularly advantageous in conjunction with Citrobacter freundii as the bacterial strain. In order not to obtain premature inhibition in process stage b), a pH-value control is appropriate. The pH-value should be in the range approximately 5.5 to 8.5. The range approximately 6.5 to 7.5 and especially a value of approximately 7 are preferred. This gives optimum biotransformation conditions for the formation of 1,3-propane diol from glycerol.

There is a quantitative matching of the H-donor and glycerol for further optimization of the process. The precise numerical values for this are dependent on the nature of the H-donor and the nature of the chosen bacterial strain. No general guideline can be given. In the case of the preferably used bacterial strain Citrobacter freundii and an H-donor in the form of glucose, between the glucose and the glycerol the preferred molar ratio is approximately 1:7 to 1:8. The molar ratio between the glucose and the glycerol could generally be with respect to practical advantages approximately 1:1 to 1:25, in particular 1:5 to 1:10.

Process stage b) is also preferably performed in a mineral medium. In order to achieve the process objective in an optimum manner, a certain part is played by the glycerol concentration in the medium of process stage b). Excessive glycerol concentrations inhibit the participating enzyme systems. Inadequate glycerol concentrations lead to undesirably high processing costs. An approximately 0.2 to 1.5 molar glycerol solution and especially an approximately 1 molar glycerol solution is optimum for the medium treated during process stage b).

The invention can undergo further per se known modifications without any variation to the essence thereof. For example reference is made to the following:

Process stage a): modification of the mineral culture medium with regards to the concentrations of the individual components; concentration of the glycerol, whereby the source-dependent impurities can differ widely as regards nature and concentration; nature of the thorough mixing of the culture medium by stirring, pumping or gassing; provision of anaerobic conditions by reducing agents and inert gases. Process stage b):

concentration of the biomass; operating pH and temperature; nature or refeeding glycerol; nature and concentration of the H-donor.

The process according to the invention has numerous advantages compared with the hitherto known processes. As a result of the two-stage process performance, i.e. growth phase in a first process stage with transfer into a stationary phase and subsequent biotransformation phase, the 1,3-propane diol yield can be raised to over 90%. If the biomass formed in the first process stage is immobilized and introduced into a column, this permits a long-term, continuous process performance, e.g. for more than 40 days. The glycerol is specifically converted into 1,3-propane diol and by-products are obtained in an unobjectionably small quantity. In certain cases they can be acetate and lactate, which can be simply removed and are not prejudicial to the environment. It is also possible to use an inexpensive nutrient medium in process stage a). In both stages, comparatively high glycerol concentrations can be chosen in the medium used. It is not necessary to abide by a particular purity of the starting glycerol. It is in fact also possible to use technical glycerols, provided that they contain no by-products disturbing the microorganisms (technical glycerols or raw glycerols). It may be the case that the technical glycerol in question is not suitable for process stage a), so that then purer glycerol starting materials would have to be used, whereas the less pure product can be used in the second process stage. This also represents an important advantage, because for the formation of the stationary phase or the biomass needed for the second process stage, a comparatively small glycerol quantity is required compared with the second process stage. This permits a more flexible performance of the process.

The invention is explained in greater detail hereinafter relative to an example.

EXAMPLE

The course of process sequence a) is shown in FIG. 1. *Citrobacter freundii* is allowed to grow in the following mineral medium under ammonium limitation: $KH_2PO_4$, 6 g/l; $K_2HPO_4.3H_2O$, 14 g/l; $(NH_4)_2SO_4$, 0.4 g/l; $MgSO_4.7H_2O$, 0.2 g/l; $CaCl_2$, 0.1 g/l; Cystein.HCl, 0.1 g/l; trace element solution (1 l contains 5 g EDTA (disodium salt), 0.3 g $H_3BO_4.4H_2O$, 0.03 g $MnCl_2.4H_2O$, 0.02 g $CoCl_2.6H_2O$, 2 g $FeSO_4.7H_2O$, 0.1 g $ZnSO_4.7H_2O$, 0.03 g $NaMoO_4.2H_2O$, 0.02 g $NiCl_2.6H_2O$, and 0.01 g $CuCl_2.2H_2O$) (cf. Arch. Microbiol., 1966, 55, 245–256), 1 ml/l; $CoCl_2$, 550 μg/l, glycerol 880 mmol/l. Following inoculation (20 ml preculture/1.2 l of main culture) incubation took place at 37° and a pH-value kept constant at 7.5. After 20 hours the culture passed into the stationary phase, in which glycerol is further reacted to 1,3-propane diol.

Figure 2:
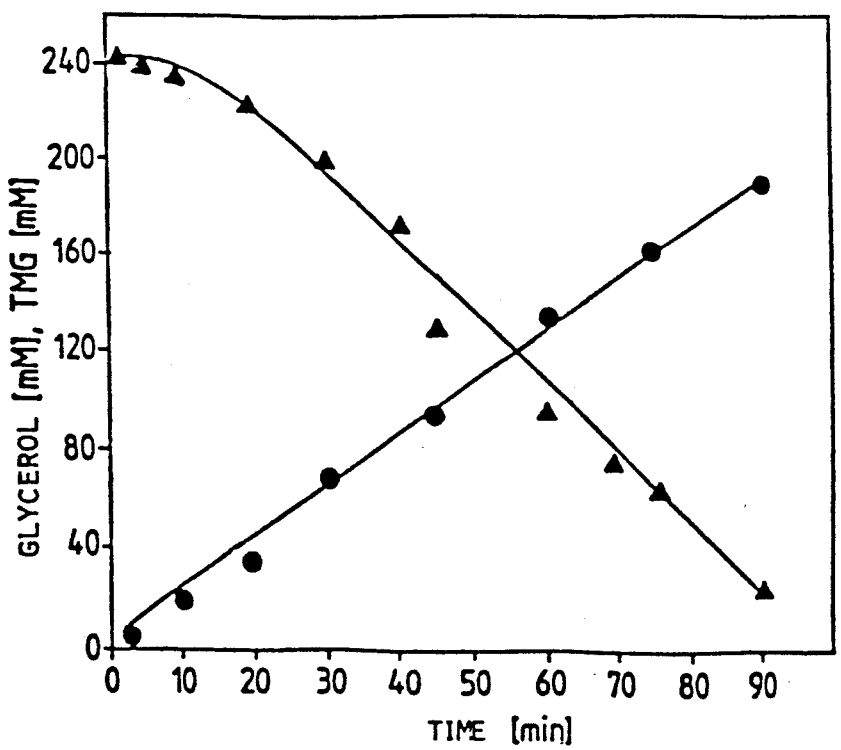

The reaction of glycerol to 1,3-propane diol in the presence of glucose as the H-donor through the cell suspension of *C. freundii* according to process stage b) is shown in FIG. 2. In this case cells were suspended in potassium phosphate buffer of pH 7.5 in a concentration of 3 mg dry weight/ml. Incubation took place in the absence of oxygen ($N_2$ atmosphere) at 37° C. after adding 240 mmol/l of glycerol and 42 mmol/l of glucose. The pH-value was held at 7.5 by means of titration with 2N KOH. 191 mmol of 1,3-propane diol were formed from 211 mmol of glycerol, i.e. 91% on molar base and 75% on a weight base (maximum possible value 83%).

Explanations concerning FIGS. 1 and 4:

FIG. 1. The course of TMG production from glycerol in ammonium-limited, static culture in the presence of an 11 times increased $Co^{2+}$ concentration. The TMG production and growth were followed in a 1.2 l culture in mineral medium with 0.04% ammonium sulphate, 880 mM glycerol and 550 μg $Co^{2+}$/l, the pH being kept constant at 7.5. Apart from TMG (▼), acetate (□), ethanol (▲), lactate (●) and pyruvate (∇) were formed. The optical density is (■) and glycerol (Δ).

FIG. 2 shows the course of TMG production through cell suspensions whilst maintaining the pH-value constant by means of KOH titration. TMG production from glycerol in the presence of 42 mM of glucose was followed through dilute cell suspensions (3 mg/ml) in $KPO_4$ buffer at pH 7.5. The pH-value was kept constant by means of titration with 2N KOH. Glycerol (▲) and TMG (●) in the presence of KOH.

FIG. 3: Comparison of TMG production from glycerol through stationary cells at different constant pH-values. The tests were performed in 4 ml cell suspensions (protein concentration: 1.8 mg/ml) at constant pH-values of 6.6 (A), 7.0 (B), 7.9 (C) and 8.0 (D). The pH-value was kept constant by titrating with 0.6N NaOH. Buffer used 248 mM $KPO_4$ (A-C) and 100 mM tris/HCl (D).

Glycerol (▲), TMG (●), acetate (■), ethanol (▲).

FIG. 4: Comparison of TMG production from glycerol through stationary cells in the absence (A) or presence (B) of glucose. The course of TMG production from glycerol by cell suspension (protein concentration: 2.4 mg/ml) in $KPO_4$ buffer was followed at a constant pH-value of 7.5. Mixture B also contained 84 mM of glucose.

Glycerol (▲), TMG (●), glucose (□).

We claim:

1. In a process for the microbiological preparation of 1,3-propanediol by cultivating in a growth medium containing glycerol and a bacterial strain which is able to convert the glycerol into 1,3-propanediol and isolating the 1,3-propanediol thus obtained, the improvement which comprises the steps of:
    (i) forming a biomass by culturing a bacterial strain from the Citrobacter genus in the growth medium containing glycerol, wherein the formation of the biomass is carried out with the substantial exclusion of any H donor;
    (ii) permitting the bacterial cells to reach a stationary cell phase;
    (iii) thereafter adding to said biomass additional glycerol and a sugar as an H-donor to the biomass, while keeping the cells in essentially a stationary phase; and
    (iii) then isolating the 1,3-propanediol thus prepared.

2. The process according to claim 1 wherein said strain is a strain of *Citrobacter freundii*.

3. The process according to claim 1 wherein step (i) is performed under anaerobic conditions.

4. The process according to claim 1 wherein step (ii) is preformed under anaerobic conditions.

5. The process according to claim 1 wherein a pH-value of approximately 6.5 to 8.5 is maintained in steps (i) and (iii).

6. The process according to claim 1 wherein steps (i) and (iii) are performed in a mineral medium.

7. The process according to claim 1 wherein step (i) is concluded by the addition of a predetermined quantity of phosphate or nitrogen source.

8. The process according to claim 7 wherein an ammonium salt is used as the nitrogen source or a potassium dihydrogen phosphate is used as the phosphate source.

9. The process according to claim 1 wherein glycerol is initially present in step (iii) in the amount of 0.2 to 1.5 molar concentration.

10. The process according to claim 1 wherein glycerol is initially present in step (i) in approximately 0.1 to 0.4 molar concentration.

11. The process according to claim 1 wherein said biomass obtained in step (i) is immobilized before step (iii).

12. The process according to claim 11 wherein said immobilization is carried out with calcium alginate.

* * * * *